United States Patent [19]

Abdallah et al.

[11] 4,134,992

[45] Jan. 16, 1979

[54] NAPHTHALENE ACETAMIDINES AS ANXIOLYTIC ANTIDEPRESSANTS

[75] Inventors: Abdulmuniem H. Abdallah; Philip J. Shea, both of Midland, Mich.

[73] Assignee: The Dow Chemical Company, Midland, Mich.

[21] Appl. No.: 821,886

[22] Filed: Aug. 4, 1977

Related U.S. Application Data

[63] Continuation of Ser. No. 736,012, Oct. 27, 1976, abandoned, which is a continuation-in-part of Ser. No. 510,957, Oct. 2, 1974, abandoned.

[51] Int. Cl.$^2$ ............................................. A61K 31/155
[52] U.S. Cl. ..................................................... 424/326
[58] Field of Search ......................................... 424/326

[56] References Cited
PUBLICATIONS

Craver et al., J. Pharm. Exptl. Therap., 99, 353 (1950).

*Primary Examiner*—Stanley J. Friedman

[57] ABSTRACT

A method useful for alleviating central nervous system depression and anxiety symptoms comprises administration to animals of an effective amount of an N,N'-dialkyl-2-naphthalene acetamidine. Compositions useful in practicing the method are also disclosed.

14 Claims, No Drawings

NAPHTHALENE ACETAMIDINES AS ANXIOLYTIC ANTIDEPRESSANTS

CROSS REFERENCE TO RELATED APPLICATIONS

This is a continuation of application Ser. No. 736,012 filed Oct. 27, 1976 which in turn is a continuation-in-part of application Ser. No. 510,957 filed Oct. 2, 1974 both are now abandoned.

The amidine compounds used in this invention can be prepared by reacting a substituted 2-naphthylacetonitrile, with excess alkylamine and alkylammonium salt at 140°–180° C. under superatmospheric pressure, as described in a commonly assigned, concurrently-filed application by James R. McCarthy, Jr. entitled N,N'-DISUBSTITUTED NAPHTHALENEACETAMIDINES, Application Ser. No. 510,956, filed Oct. 2, 1974, now U.S. Pat. No. 3,903,163.

BACKGROUND OF THE INVENTION

The substituted amidine compounds of the invention can be prepared by a modification of known methods. Typical methods which can be so modified include the reaction of a nitrile with a trialkyloxonium fluoroborate to prepare an N-alkyl nitrilium salt in a procedure similar to that of Meerwein et al., Ber. 89, 209 (1956), Borch, J. Org. Chem., 34, 627 (1969), and Weintraub et al., J. Org. Chem. 33, 1679 (1968). The nitrilium salt is then reacted with a primary alkylamine to obtain the amidine. A number of N-monosubstituted and unsubstituted amidines are known. Craver et al., J. Pharm. Exptl. Therap. 99, 353 (1950); Netherlands Application No. 6,508,754, C.A. 65, 2181c (1966); U.S. Pat. Nos. 3,344,138, 3,417,122 and 3,334,137. b-Naphthamidine is disclosed by Markwardt et al., Pharmazie 1969 24(7), 400–2.

SUMMARY OF THE INVENTION

This invention is directed to a method which comprises administering to a mammal an effective antidepressant or anxiolytic amount of substituted naphthalene acetamidine compound or a pharmacologically-acceptable salt thereof, or a composition containing such substituted acetamidine compound or salt as the active antidepressant-anxiolytic ingredient therein; said substituted naphthalene-acetamidine compound corresponding to the formula:

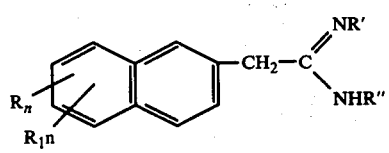

wherein R and $R_1$ each independently represent halo, lower alkyl or lower alkoxy; n independently in each occurrence represents zero or one; and R' and R" each independently represent a loweralkyl substituent.

It has been found that the 2-naphthalene acetamidines, of the above formula and their pharmacologically-acceptable salts have potent antidepressant and anxiolytic properties. (For the purpose of brevity, such compounds will be hereinafter referred to as "substituted amidines".) Administration of one or more of the substituted amidine compounds to mammals has been found to provide valuable antidepressant effects accompanied by anxiolytic or calming effects, thus providing for alleviation of central nervous system depression without accompanying central nervous stimulation or agitation; and in a corresponding manner, providing alleviation of symptoms of anxiety or nervous agitation without accompanying detrimental depressant effects. The compounds have exhibited little or no significant detrimental pharmacological effects at dosages consistent with good antidepressant-anxiolytic activity, and are notably lacking in significant cardiovascular effect on blood pressure, as well as having little or no anticholinergic effects.

The substituted amidine compounds are crystalline solids which are soluble in a variety of conventional liquids, including alcohols, chlorinated hydrocarbons, etc. In general, the pharmacologically-acceptable salts are more soluble in aqueous liquids than are the free base compounds, and the substituted amidines are preferably employed in the form of such salts.

As employed herein, the phrase "pharmacologically-acceptable salt" refers to salts of the substituted amidines, the anions of which are relatively non-toxic and innocuous to mammals at dosages consistent with good antidepressant activity so that side effects ascribable to the anions do not vitiate the beneficial effects of the substituted amidines. Suitable pharmacologically-acceptable salts which can be employed in the method and composition of the invention include those derived from mineral acids such as the hydrochloride, hydrobromide, phosphate, nitrate and sulfate salts, those derived from organic carboxylic acids such as the succinate, tartrate, citrate, malate, maleate, and acetate salts and those derived from organic sulfonic acids such as the methanesulfonate and toluenesulfonate salts. Hydrohalides, such as the hydrochloride salts, are preferred.

In practicing the method, one or more substituted amidine is administered internally to a mammal by a route effective to introduce an effective amount of the compound into the blood stream of the mammal. Administration can be carried out either by a parenteral route such as by intravenous, intraperitoneal, subcutaneous or intramuscular injection, or by introduction into the gastrointestinal tract by oral administration, for example, to introduce the compound into the blood stream via the gastrointestinal tract. The substituted amidines are orally effective, and generally have a higher ratio of toxic dose to effective dose when orally administered, and this route is preferred.

The effective amount of substituted amidine to be administered can also be referred to as an "antidepressant amount" (amount sufficient to alleviate central nervous system depression); as an "anxiolytic amount" (amount sufficient to alleviate symptoms of anxiety, i.e., symptoms of central nervous system agitation); or as an "antidepressant-anxiolytic amount", since the dosage sufficient to provide antidepressant effect also provides some anxiolytic effect, and vice-versa. In the present specification, the terms can be regarded as interchangeable with respect to dose.

The antidepressant-anxiolytic amount of compound, that is, the amount of the substituted amidine compound sufficient to provide the desired effect depends on various known factors such as the size, type, age and condition of the animal to be treated, the particular amidine or pharmacologically-acceptable salt employed, the route and frequency of administration, the type and degree of central nervous system condition involved, the time the compound is administered relative to prior and subsequent presentation of food and liquids, etc. In particular cases, the dosage to be administered can be ascertained by conventional range finding techniques, for example, by observing the effect produced at different dosage rates.

Generally, the compound is administered at dosage rates from about 1 to about 4 to about 25 to about 50 milligrams of substituted amidine compounds per kilogram of animal body weight. Higher dosage rates may be employed, for example, when the compound is administered orally in a timed release dosage form. When administered by injection, good results are obtained with an amount of from about 1 to about 25 milligrams of the amidine compound per kilogram of animal body weight. From about 1 to 120 milligrams of the amidine compound per kilogram, depending on dosage unit form employed, provide good results when the compounds are administered orally. In the case of mammals suffering from central nervous system depression or exhibiting symptoms of anxiety, administration of an antidepressant-anxiolytic amount of the substituted amidine compound is preferably repeated at predetermined intervals to provide a substantially continuous effect. It is generally desirable to administer the individual dosages at the lowest antidepressant-anxiolytic amount which provides the desired continuity consonant with a convenient dosing schedule. In a convenient repetitive procedure, the substituted amidines are administered in single or divided oral doses at daily rates of about 1 to 150 milligrams per kilogram per day.

In practicing the method of the invention, the active ingredient is preferably incorporated in a composition comprising a pharmaceutical carrier and from about 0.001 to about 95 percent by weight of the substituted amidine compound or a pharmacologically acceptable salt thereof. The term "pharmaceutical carrier" refers to known pharmaceutical excipients useful in formulating pharmacologically-active compounds for internal administration to animals, and which are substantially non-toxic and non-sensitizing under conditions of use.

Suitable pharmaceutical carriers are known and disclosed in texts such as Remington's Pharmaceutical Sciences, Thirteenth Ed., Martin (Ed.) Mack Publishing Co., Easton, Pa. (1965). The compositions can be prepared by known techniques for the preparation of tablets, capsules, lozenges, troches, elixirs, syrups, emulsions, dispersions, wettable and effervescent powders, sterile injectable compositions, and can contain suitable excipients known to be useful in the preparation of the particular type of composition desired.

Dosage units adaptable to oral administration such as tablets, capsules, lozenges, elixirs, syrups and the like are preferred and the active amidine compound can be formulated in conventional timed release capsule or tablet formulations.

Preferred compositions include sterile injectable solutions containing from about 0.001 to about 10 percent by weight of the amidine compound in a pharmaceutical carrier suitable for injection, such as isotonic saline solution, Ringer's Injection USP, and lactated Ringer's USP, and the like. Preferred compositions for oral use include unit dosage forms such as capsules and compressed tablets, containing a pharmaceutical carrier and from about 1 to about 150 milligrams of amidine compound per unit.

The following examples are illustrative of the invention.

EXAMPLE 1

Separate groups of mice of the same origin and past history (5 mice per group) were administered N,N'-dimethyl-2-naphthalene acetamidine hydrochloride as a sterile injectable composition. Different groups were administered the compound by intraperitoneal injection at dosage rates of 10, 21.5 and 46 grams of test compound per kilogram of animal body weight. Thirty minutes after the administration of the test compounds, the mice were administered reserpine at a dosage rate of 2.5 milligrams per kilogram by intraperitoneal injection. Separate groups of similar mice were similarly administered 2.5 milligrams of reserpine per kilogram 30 minutes after administration of various dosages of the known antidepressant. The mice were then observed for 45 minutes for symptoms of reserpine-induced depression.

In repeated prior check observations, the administration of 2.5 milligrams per kilogram of reserpine intraperitoneally to mice has been observed to result in a classical progression of symptoms beginning with a characteristic dropping of the eyelids (ptosis) and later culminating in a generalized depression with decreased spontaneous motor activity and decreased responsiveness to auditory and tactile stimuli. Protection from reserpine-induced depression is indicated by the absence of the characteristic ptosis.

The results were employed to calculate the dose effective to protect 50 percent of the mice ($ED_{50}$) by classical statistical procedures. The amidine compound was found to have an $ED_{50}$ of 12.6 mg/kg, with 95 percent fiducial limits from 7.8 to 20.5, and desipramine hydrochloride was found to have an $ED_{50}$ of 19.0 (7.1–50.9 95% fiducial limits).

EXAMPLE 2

The procedure of Example 1 was repeated, using oral administration of 10, 21.5 or 46.4 milligrams of N,N'-dimethyl-2-naphthalene acetamidine hydrochloride instead of intraperitoneal injection. The oral $ED_{50}$ was found to be 17 to 35 mg/kg.

In a similar operation carried out with rats as the test animals, the oral $ED_{50}$ was found to be 34.8 mg/kg.

EXAMPLE 3

Mice were divided into groups and were placed individually in cages. After 30 minutes, rectal temperatures were recorded, and each mouse was administered reserpine (2.5 mg/kg i.p.). Administration of this dosage of reserpine results in marked hypothermia of several hours' duration. Three and one-half hours after reserpine adminstration, one group of mice was administered N,N'-dimethyl-2-naphthaleneacetamidine hydrochloride in a saline injection solution carrier (i.p., 21.5 mg/kg). A separate group was administered an equal amount of saline carrier, with no test compound. Rectal temperatures were recorded 30, 60 and 90 minutes after injection. The mice administered 21.5 mg/kg of the test compound were found to exhibit reversal of hypothermia, with mean body temperatures of 34–35° C. during the test period, while those administered saline show decreasing mean body temperatures from about 33 to about 33.5° C. during the same period.

EXAMPLE 4

Calmative or anxiolytic effect is evaluated in a procedure similar to the electric shock induced aggression procedure of Tedeschi et al., J. Pharm. Exptl. Therap. 125, 28–34 (1959). Aggression and fighting are induced in pairs of mice by mild foot shock (3 milliamperes, 0.2 seconds duration, 3 shocks per second) applied to a cage floor grid over a two minute period. The number of fighting episodes is counted during the two minute period, and aggression recorded as present or absent if fighting episodes are more or less than the mean number of episodes, plus or minus 1.5 standard deviations, obtained with mice administered only saline solution. In this procedure, N,N'-dimethyl-2-naphthaleneacetamidene hydrochloride, administered by intraperitoneal injection in sterile saline solution, is found to inhibit aggression with an $ED_{50}$ of 12.6 milligrams per kilogram. The known anti-anxiety (anxiolytic) agents diazepam, chlordiazepoxide and chlorazepate dipotassium also inhibit aggression in this procedure, with i.p. $ED_{50}$'s between 4 and 30 mg/kg.

EXAMPLE 5

In other operations with the test compound, N,N'-dimethyl-2-naphthaleneacetamidine hydrochloride, a number of other pharmacological evaluations are carried out.

The test compound is found to have no effect on pentylenetetrazole induced convulsions at i.p. dosages up to 46.4 mg/kg and no effect on tryptamine induced convulsions in rats.

The test compound is found to have no significant effect on total spontaneous motor activity of mice at i.p. dosages of 4.64 and 10 mg/kg and a depressant effect at a dosage of 21.5 mg/kg. It is also found to have no effect on behavior of mice trained to avoid electric shock administered via a cage floor grid by jumping to a platform, at i.p. dosages of 10, 21.5 and 46.4 mg/kg. After feeding to male mice for five weeks at rates of 0.025 and 0.05 percent in the food, no significant effects on body weight, food intake or total spontaneous motor activity are observed.

The test compound is found to potentiate symptoms of hyperexcitability, fighting and death induced by subcutaneous injection of 20 mg/kg of yohimbine hydrochloride in aggregated mice, with an $ED_{50}$ of 0.8 mg/kg (i.p.) when administered 30 minutes prior to yohimbine challenge.

In other operations, the compound is found to inhibit norepinephrine uptake; to lack both significant monoamine oxidase inhibition activity and significant anticholinergic activity; and to potentiate the stimulant effect of levodopa. In the dog, the test compound exhibits no appreciable effect on blood pressure when administered intravenously, and, like known tricyclic antidepressants, to attentuate the pressor response to tyramine.

EXAMPLE 6

N,N'-Dimethyl-2-naphthalene acetamidine hydrochloride was administered intragastrically to separate groups of five rats each at dosage rates of 50 and 100 mg/kg/days for thirty days. On the thirtieth day, 2.5 mg/kg of reserpine was administered intraperitoneally, thirty minutes after the test compound was administered, and absence of reserpine induced ptosis was observed at 75 and 90 minutes after reserpine. Inhibition of ptosis was observed in all rats treated with 100 mg/kg/day of the test compound, and in four of the five rats administered 50 mg/kg/day. Separate groups of rats were similarly dosed for 30 days with the test compound, and on the thirty-first day, were starved for 18 hours prior to test compound dosing and reserpine challenge. Inhibition of ptosis in the starved rats was observed in all rats at the 100 mg/kg/day dose level and in 4 of the 5 rats at the 50 mg/kg/day dose level. In a separate acute test with fasted rats, inhibition of ptosis was observed in 20, 40 and 40 percent, respectively, of the rats administered 10, 21.5 and 46.4 mg/kg of the test compound intragastrically. The above results indicate that tolerance to the test compound did not develop during the test period. Weight gain and total spontaneous motor activity of the rats were not significantly affected by the 30 day dosing schedule, at either dosage rate.

EXAMPLE 7

In a 30 day operation similar to that of Example 6, the same test compound was administered to mice by daily intraperitoneal injection at dosage rates of 10, 21.5 and 46.4 mg/kg/day. Ten mice were used at each rate, and the $ED_{50}$ for inhibition of reserpine induced ptosis was determined on the thirtieth day to be 9 mg/kg (with 95% confidence limits from 4 to 21). This compares favorably with the $ED_{50}$'s determined for acute intraperitoneal administration — 11 mg/kg (95% confidence limits 6 to 22, 10 mice per dose level) and in Example 1 with five mice per dose level, indicating that tolerance did not develop.

EXAMPLE 8

In reserpine antagonism operations similar to those of Examples 1, 2 and 3, the following compounds are found active in one or more test: N,N'-dimethyl-1-chloro-2-naphthalene acetamidine · HCl; N,N'-diethyl-1-chloro-2-naphthalene acetamidine · HCl; N,N'-dimethyl-6-methyl-2-naphthalene acetamidine · HCl; N,N'-diethyl-6-methyl-2-naphthalene acetamidine · HCl; N,N'-dimethyl-6-methoxy-2-naphthalene acetamidine p-toluenesulfonate; N,N'-dimethyl-3-methyl-2-naphthalene acetamidine · HCl; and N,N'-diethyl-2-naphthalene acetamidine · HCl.

What is claimed is:

1. A method useful for alleviating symptoms of central nervous system depression and anxiety in an animal comprising administering to the animal an amount of a substituted amidine or a pharmacologically-acceptable salt thereof effective to alleviate said symptoms, the substituted amidine corresponding to the formula:

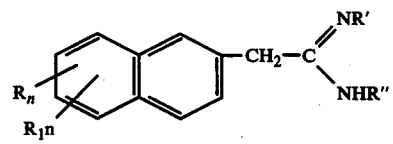

wherein R and $R_1$ each independently represent halo, lower alkyl or lower alkoxy; n independently in each occurrence represents zero or one; and R' and R" each independently represent loweralkyl.

2. Method of claim 1 where n is zero and R' and R" both represent methyl.

3. Method of claim 2 wherein the compound is N,N'-dimethyl-2-naphthaleneacetamidine hydrochloride.

4. A method useful for alleviating symptoms of central nervous system depression in an animal comprising administering to the animal an amount of a substituted amidine or a pharmacologically-acceptable salt thereof effective to alleviate said symptoms, the substituted amidine corresponding to the formula:

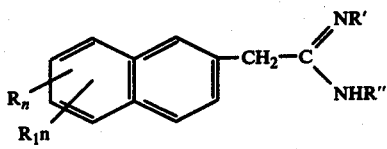

wherein R and $R_1$ each independently represent halo, lower alkyl or lower alkoxy; n independently in each occurrence represents zero or one; and R' and R" each independently represent loweralkyl.

5. Method of claim 4 wherein n is zero and R' and R" both represent methyl.

6. Method of claim 4 wherein the animal is a depressed mammal.

7. A method useful for alleviating symptoms of central nervous system anxiety in an animal comprising administering to the animal an amount of a substituted amidine or a pharmacologically-acceptable salt thereof effective to alleviate said symptoms, the substituted amidine corresponding to the formula:

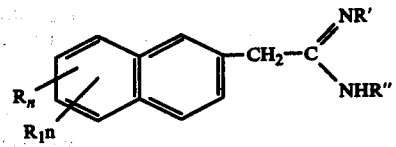

wherein R and $R_1$ each independently represent halo, lower alkyl or lower alkoxy; n independently in each occurrence represents zero or one; and R' and R" each independently represent loweralkyl.

8. Method of claim 6 wherein the animal is a mammal exhibiting anxiety symptoms.

9. A composition useful for alleviating symptoms of central nervous system depression and anxiety in an animal comprising from about 0.001 to about 95 percent by weight of a substituted amidine or a pharmacologically-acceptable salt thereof the substituted amidine corresponding to the formula:

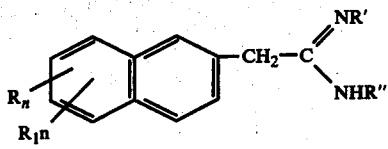

wherein R and $R_1$ each independently represent halo, lower alkyl or lower alkoxy; n independently in each occurrence represents zero or one; and R' and R" each independently represent loweralkyl and a pharmaceutical carrier therefor.

10. A composition of claim 9 wherein n is zero and R' and R" are both methyl.

11. A composition of claim 10 wherein the compound is N,N'-dimethyl-2-naphthaleneacetamidine hydrochloride.

12. Method of claim 1 wherein the substituted amidine is 1-chloro-N,N'-dimethyl-2-naphthaleneacetamidine.

13. Method of claim 4 wherein the substituted amidine is 1-chloro-N,N'-dimethyl-2-naphthaleneacetamidine.

14. A composition of claim 10 wherein the compound is 1-chloro-N,N'-dimethyl-2-naphthalene-acetamidine hydrochloride.

* * * * *